(12) United States Patent
Bertagnolli

(10) Patent No.: US 7,084,442 B2
(45) Date of Patent: Aug. 1, 2006

(54) DOUBLE GATE TRANSISTOR ARRANGEMENT FOR RECEIVING ELECTRICAL SIGNALS FROM LIVING CELLS

(75) Inventor: Emmerich Bertagnolli, Vienna (AT)

(73) Assignee: Austria Wirtschaftsservice Gesellschaft mit beschrankter Haftung, Vienna (AT)

( * ) Notice: Subject to any disclaimer, the term of this patent is extended or adjusted under 35 U.S.C. 154(b) by 0 days.

(21) Appl. No.: 10/922,545

(22) Filed: Aug. 19, 2004

(65) Prior Publication Data

US 2005/0024953 A1 Feb. 3, 2005

Related U.S. Application Data

(63) Continuation of application No. PCT/AT03/00056, filed on Feb. 19, 2003.

(30) Foreign Application Priority Data

Feb. 19, 2002 (AT) ................ A 252/2002

(51) Int. Cl.
*H01L 23/58* (2006.01)

(52) U.S. Cl. ............. 257/253; 257/252; 257/288; 257/289; 438/48; 438/49; 438/51

(58) Field of Classification Search ........ 257/252–253, 257/288, 289; 438/48, 49, 51, 54; 607/2
See application file for complete search history.

(56) References Cited

U.S. PATENT DOCUMENTS

| 4,921,591 A | 5/1990 | Mochizuki et al. |
| 5,801,428 A | 9/1998 | Felde et al. |
| 6,181,969 B1 | 1/2001 | Gord |

*Primary Examiner*—Donghee Kang
(74) *Attorney, Agent, or Firm*—Merchant & Gould P.C.

(57) ABSTRACT

The invention involves an array to couple a live cell, in particular a nerve cell, with an electronic circuit to pick up directly or indirectly electrically active cell signals and/or to electronically stimulate the cell, where the coupling array comprises a transistor (T1) with a double gate, where one of the gates is designed as a control gate (CG) to select the transistor via external control signals, and the other gate (FG) is connected to an electrically conducting contact element (1) which may be brought into contact with the cell (2) to register changes in the electric properties of the cell.

12 Claims, 12 Drawing Sheets

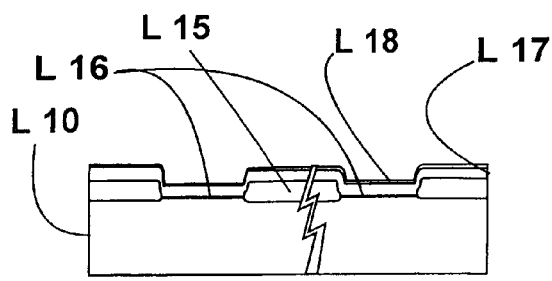
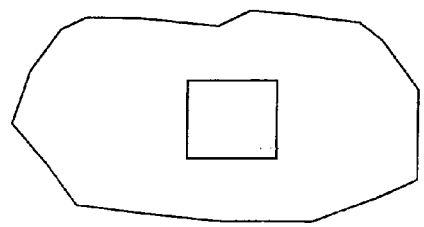
Fig. 15A   Fig. 15B
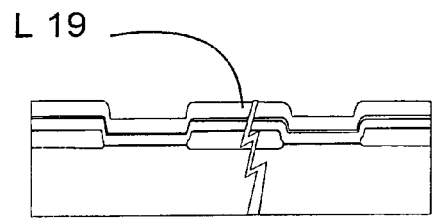
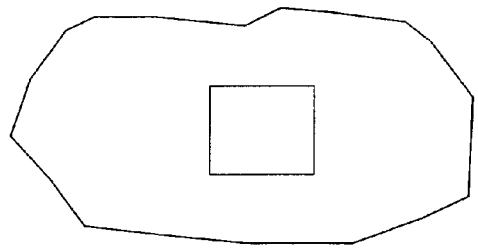
Fig. 16A   Fig. 16B
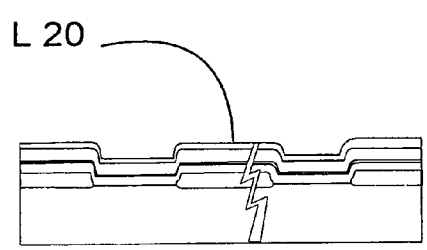
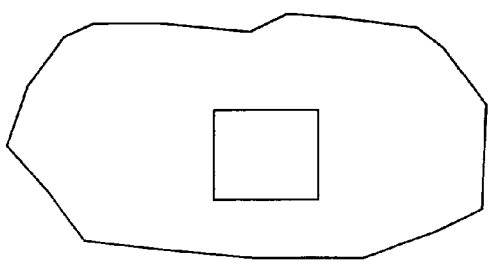
Fig. 17A   Fig. 17B
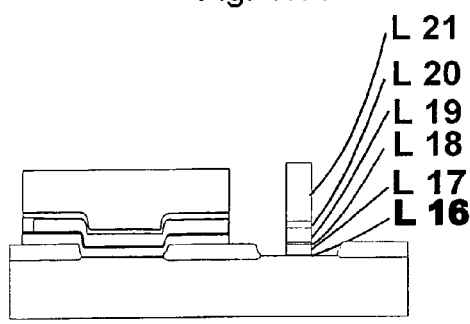
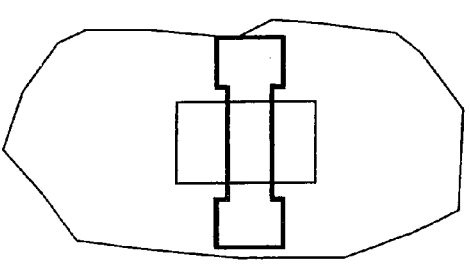
Fig. 18A   Fig. 18B

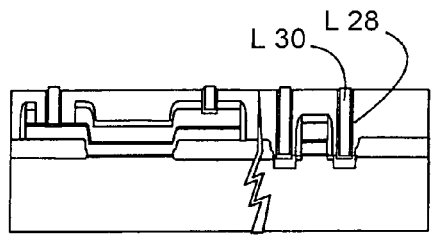
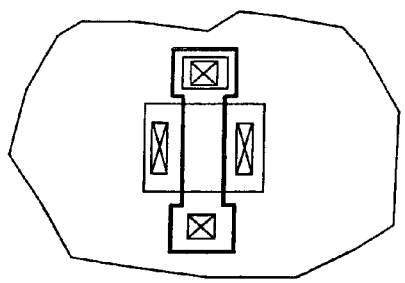
Fig. 27A   Fig. 27B
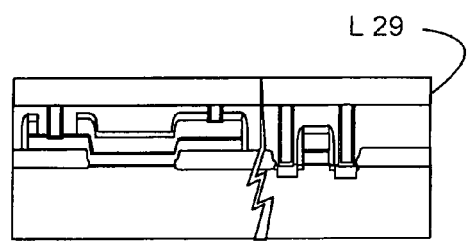
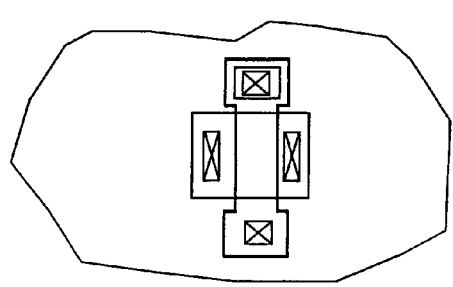
Fig. 28A   Fig. 28B
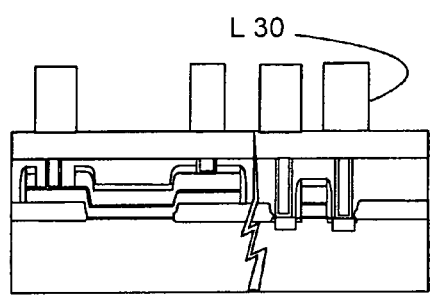
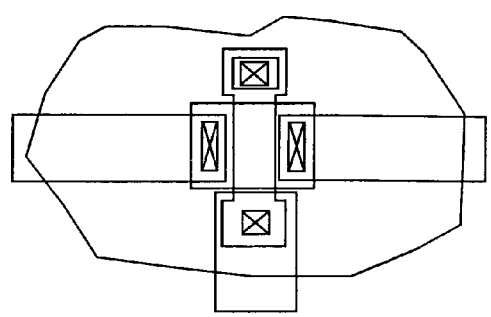
Fig. 29A   Fig. 29B
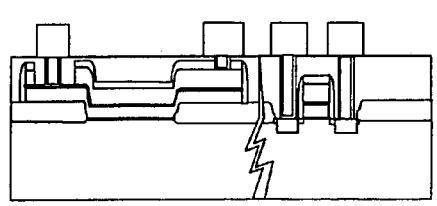
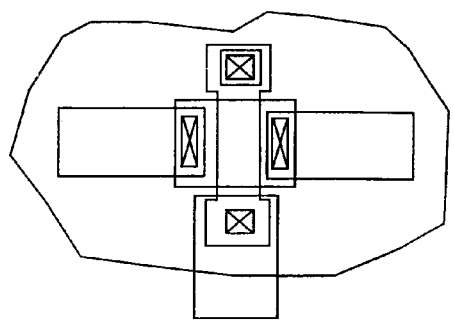
Fig. 30A   Fig. 30B

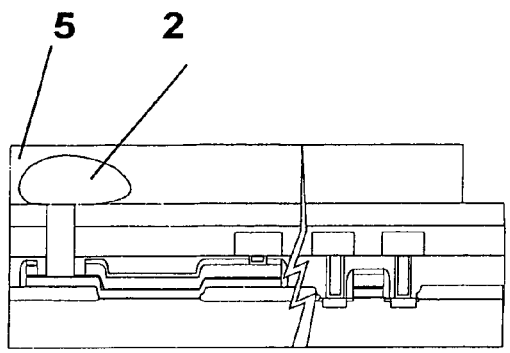 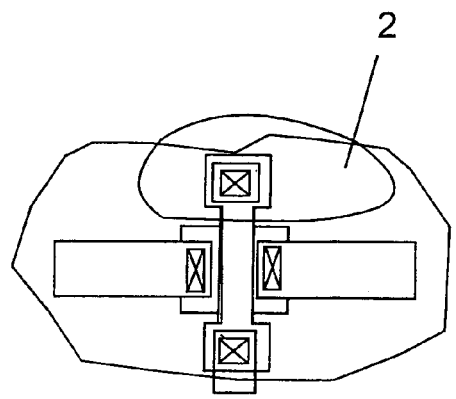
Fig. 35A    Fig. 35B
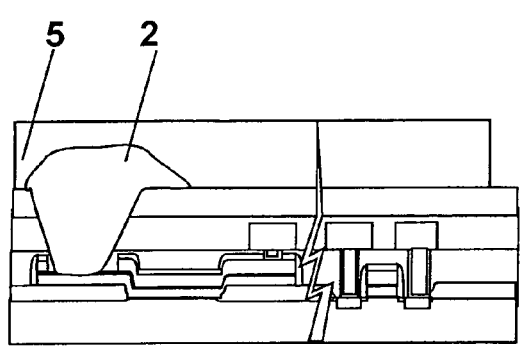 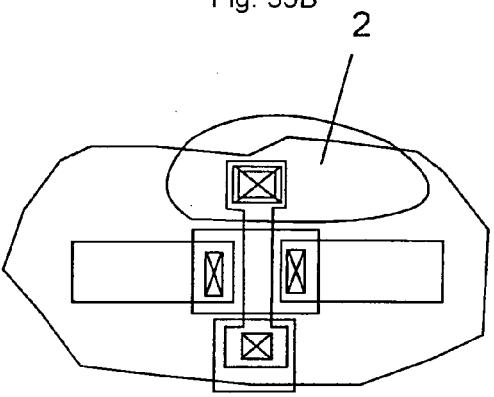
Fig. 36A    Fig. 36B
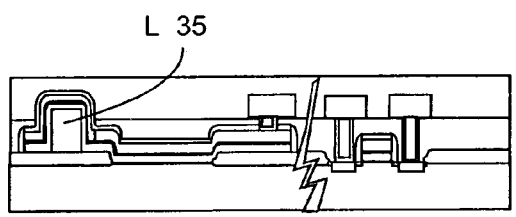 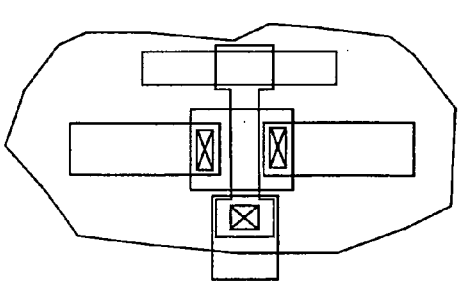
Fig. 37A    Fig. 37B
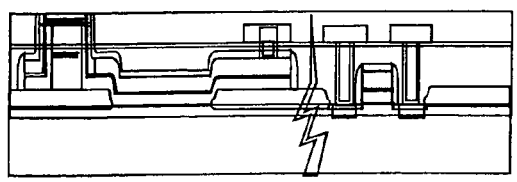 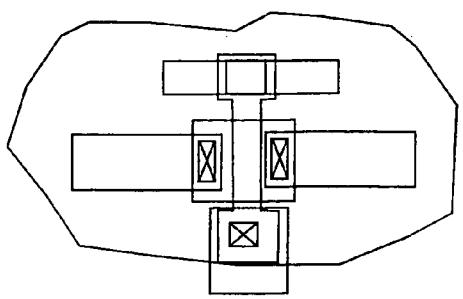
Fig. 38A    Fig. 38B

DOUBLE GATE TRANSISTOR ARRANGEMENT FOR RECEIVING ELECTRICAL SIGNALS FROM LIVING CELLS

This application is a continuation of international application number PCT/AT03/00056. filed 19 Feb. 2003, which claims priority to Austrian application Serial No. A 252/2002. filed 19 Feb. 2002, entitled DOUBLE GATE TRANSISTOR ARRANGEMENT FOR RECEIVING ELECTRICAL SIGNALS FROM LIVING CELLS, which application(s) are incorporated herein by reference.

The invention involves an array to couple a live cell, in particular a nerve cell, with an electronic circuit to pick up directly or indirectly electrically active cell signals and/or to electronically stimulate the cell.

Below an interaction of the coupling array with a cell where general, directly or indirectly electrically active cell signals, and especially electric signals emanated by nerve cells are picked up and processed is described as "passive mode". An interaction of the coupling array with a cell that causes the cell to be electrically stimulated is described as "active mode".

Without limiting the generality of the inventive approach, the invention presented may also be implemented at a large scale, i.e. on the basis of existing integration processes of micro- and nanoelectronics, where initially only such processes and materials are used that are, on the one hand, compatible with a modern manufacturing environment for silicon chips and, on the other hand, not biologically harmful. In a further development, other electronic structures that are capable of data processing, such as, i.a., organic circuits, are conceivable and feasible.

Previous processes use, on the one hand, optical methods based on the voltage dependence of colorants (e.g. fluorescence) or extra-cellular metal electrodes. On the other hand, they use invasive methods, e.g. electrodes inserted directly in the cell to detect intracellular potentials. Among the category of invasive electrodes is the silicon needle provided with photolithographically produced circuits and contacts on the tip.

The reverse function, electric stimulation of a cell, has so far been similarly performed by inserted electrodes.

In addition to the technical solutions mentioned to detect and stimulate single cells, there are the so-called cuff electrodes. This is a cuff covered by a wire net and placed around a nerve fibre (including supply and support tissue). However, cuff electrodes allow only a summary pickup and impression of potentials.

Considering that the invasive access to the cell is concomitant to an injury to or direct/indirect destruction of the cell, there is a need for high spatial and temporal resolution and electric sensitivity for non-invasive (or non-penetrating) access to the cell. This requirement is not met by any of the existing devices or methods.

Previous non-invasive solutions based on MOS transistors are inherently based on influencing the inversion layer in the channel of a MOSFET, either directly by placing the nerve cell or axon on the gate dielectric, or indirectly by placing this electrically effective cell part on the gate.

In the one case, the contact between cell and transistor is made so that part of the cell membrane is placed on or made to contact the transistor in the channel. This area is separated from the substrate by the gate dielectric, usually a natural oxide or an artificially grown oxide. Charges or changes in charges of the contacting cell or cell membrane affect the channel conductivity of the transistor. The coupling strength so far achieved with this method is in the range of a 10% change in the gate to cell membrane potential. The MOS transistor, screened off by oxide and with the exception of the leads sticking out on the sides, is completely immersed in electrolyte liquid that is enriched with a nutrient solution, which is extremely detrimental to its life (metal ions, and especially Na and K ions migrate to the gate dielectric, causing progressive degradation). In addition, partially formed channels of variable or weak coupling will be formed, not least due to the incomplete screening of the channel area.

For such reasons, this approach offers only a limited solution for a few single interfaces between the tissue and the electronic system. In view of the lack of regular wiring options for the transition, this solution allows only a limited number of scanning cycles, and on-site amplification and processing of signals is subject to difficult marginal conditions.

Furthermore, this system precludes any direct actuator stimulation.

Another known approach is based on the coupling of a neuron to an MOS gate based on a direct metal galvanic contact between the cell membrane and transistor gate. Here again, the measuring principle is based on the influence on the MOSFET channel exerted by the charge of the gate. Here, an advantage is enjoyed in that the sensitive gate oxide need not be exposed directly to the nutrient solution so that this system can be expected to have a longer useful life.

In both cases, the selection principle is based on the use of differential amplifiers (generally of the CMOS type) to detect changes in conductivity of the contact transistor compared to a non-contacted regular transistor.

In order to stimulate the cell, separate stimulation circuits and suitable contact configurations are required in both cases, e.g. by running ring contacts around the contact transistor.

The present invention seeks to find a solution for the disadvantages of the current state of the art as described above.

In order to meet this object, an array is provided to couple a live cell, in particular a nerve cell, with an electronic circuit to pick up directly or indirectly electrically active cell signals and/or to electrically stimulate the cell in accordance with the characterising features of Claim 1. Beneficial developments of the invention are described in the sub-claims.

In contrast to all previously known approaches, this coupling array according to the invention allows both the solely passive picking-up of directly or indirectly electrically active cell signals as well as the direct active electric stimulation and influencing (activation) of the cell. The selection of passive or active operating mode is made by an external switch and the choice of voltages and currents applied. Addressing and retrieval are passive only, i.e. they do not change the potential or electric state of the cell.

The invention may be applied in particular to the following subject areas:

Studies of directly or indirectly electrically active activities of cells and mechanisms of propagating the impulse of action potentials along axons (nerve fibres).

Signal processing in networks of live neurons.

Simultaneous detection, listed by place and time, of the response to signals/stimulation by a large number of cells/neurons and the associated study of electric wiring of cells/neurons.

Building or assembling of biosensors, in particular neuronal biosensor or sensor/actuator systems and arrays.

Implementation of neuron-electronic circuits.

Other possible applications of the invention concern the design of sensoric and sensomotoric actuators and receptors for prostheses and the implementation of electronic substitutes for nerve fibres, especially for damaged or cut nerve fibres.

In addition, the invention offers an opportunity to study the effect of chemical and physical stimuli, and especially of medicinal drugs and bioactive media on the function and functioning of cells, tissues and tissue parts.

The basic idea of the invention is based on contacting a live cell with a gate of a double-gate transistor, so that any change in the electric properties of the cell or part thereof will control the transistor's behaviour, which can be electrically picked up by a selection circuit. This circuit also allows to apply electric signals or stimuli to this cell or part thereof.

In the long term, biological cells can survive only when they are kept in a liquid environment, generally in a so-called nutrient solution. Accordingly, the structure of the circuit according to the invention should allow the biological cell to be placed in a liquid. According to the invention this is ensured by the provision of a container for the nutrient solution into which container at least one contact element projects or constitutes at least part of the inside.

In order to ensure a defined measuring potential, a development of the invention provides for an electrically conducting reference electrode connected to a reference voltage, which electrode projects into the interior of the nutrient solution container.

A long useful life of the coupling array according to the invention and minimal influence on the cells thus coupled may be achieved when the electrically conducting contact element comprises a material of low biological effect, preferentially chosen from refractory metals such as platinum, iridium, osmium, tungsten or gold or alloys thereof; or from semiconductor silicides such as platinum silicide, tungsten silicide, titanium silicide; or from a doped monocrystalline or polycrystalline semiconductor such as conductive polysilicon; or from conductive synthetics.

Notwithstanding the simplicity of the embodiments schematically shown, the coupling array according to the invention is limited neither to single cells nor to cells kept in a liquid.

Rather, the array is excellently suitable to electrically couple entire cell clusters, cell unions, or even entire functional cell units or combinations thereof. In such case, contact fields rather than single contacts are arrayed in the liquid container which are each connected and linked electrically according to the invention.

With regard to storing cells, cell clusters, functional cell groups or combinations thereof in a liquid/nutrient solution it must be noted that any aqueous environment, including specifically body or tissue liquids, suffices to achieve an electrolytic coupling.

In a useful development of the invention, a range of coupling arrays is arranged in the form of a matrix of lines and columns, where the input of each electronic switch is connected to a column address circuit and a controlling connection of the electronic switch is connected to a line address circuit.

Furthermore an addressing circuit may be provided for single or group application of supply or signal voltages on column address circuits and of control voltages on line address circuits. Thus, if the matrix shows a structure in the form of i lines and j columns, the function of the i/jth element allows a unequivocal allocation on the cell field assigned to the matrix. If a number of cells, e.g. nerve cells, is brought into contact with such a matrix, then the cells can be contacted individually and signals can be exchanged in the passive or active mode. Due to the particularity of the accepting circuit, i.e. the matrix form, the electric signals can—as described above—be allocated locally. With this, it is possible to determine and contact individual active cells of a more or less large number of cells which may, e.g. constitute a functional union. Such a contact may be either solely in the passive mode, or in the active mode, or, optionally, in both modes alternatively.

If a larger-scale cell ensemble is placed on one or more such matrix-shaped cell fields of electronic single cells, it is possible by activating electronic retrieval (passive/active mode) to determine which type of contact is present on which site, what is the spatial configuration of such contacts and how a signal sequence corresponding to a given application purpose or an algorithm is to be applied.

In this manner, non-active or insufficiently active or non-contacted cells may be similarly determined and may, e.g., be excluded from further interactive processing (passive and/or active mode), through the address circuit having address evaluation tools to detect dysfunctional cells and faulty contacts between the contact element and the cell, where in the case of such detection, if need be, further interaction of such cells or contact elements may be selectively interrupted. For the selective interruption of cell interaction, interruption tools, such as electronic switches, may be provided.

The coupling array according to the invention permits arranging a large number of coupling arrays on a chip, where the chip is preferentially made of Si-planar technology and may be integrated with other technologies, such as circuits for local amplification, on-chip logic or systems on chips (SoC).

The component density achievable today in accordance with the state of the art permits the design of very large arrays of cell sensors and actuators, where local electronic circuits may optionally be accommodated at any node of such an array. This may be necessary in the case of low signal intensity (e.g. the lift of a cell membrane voltage on activating a nerve cell typically is <60 mV) or if noise sources or noise levels occur.

Using this sensor array and suitable address circuits, it is possible to observe/measure the signal propagation and processing in biological cells, cell clusters and functional cell systems, particularly in nerve cell tissues, and if necessary data thus obtained may be further processed.

In another development of the invention, the nutrient solution container is arranged on the chip. This allows entire cell clusters, cell unions or even entire cell units or combinations thereof to be stored in liquid within contact range of the contact elements and enables the chips to be used in an aqueous environment, specifically also in body or tissue liquids that permit electrolytic coupling. In this development, the top layer of the chip, the so-called passivation, is to be designed so that the contact points or contact surfaces of the contact elements are attached to special penetration points and these are then brought into contact with the cells.

The coupling array according to the invention can be placed directly in live tissue or openings thereof. For contact with the tissue liquid, the electrolyte, a suitable contact, possibly also integrated, is to be provided according to the invention.

Below, embodiments of the invention are described with reference to the drawings. However, the invention is not limited to these embodiments.

Of the drawings, FIG. 1 shows a schematic diagram of a coupling array according to the invention, with a double-gate transistor as an electric coupling element.

FIGS. 7 to 33 show a process according to the invention for producing a coupling array according to the invention with a double-gate transistor as the electric coupling element.

FIGS. 34 to 41 show various variants of the coupling array according to the invention with a double-gate transistor.

In the description below, identical or similar elements are described with the same reference number so that it will not be necessary to repeat the description of such elements.

FIG. 1 shows a schematic diagram of an array according to the invention for the electric coupling of a biological cell 2 to this array.

Figure 1:
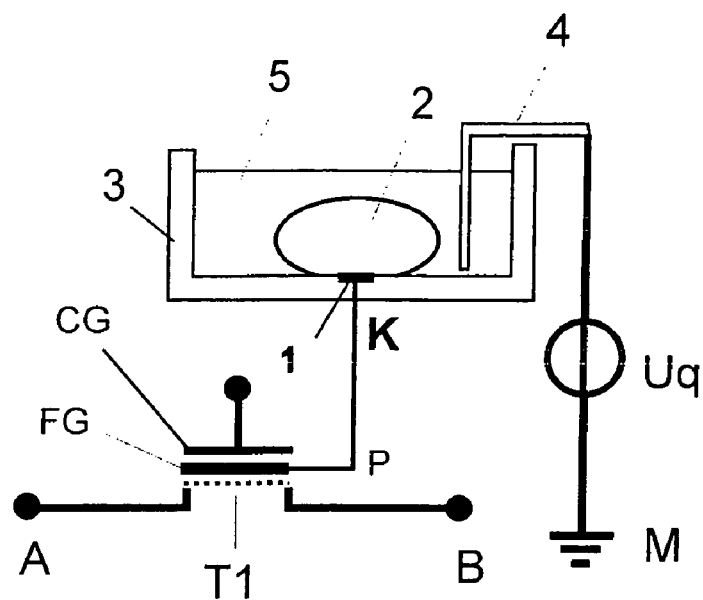

The live cell 2 is placed in a nutrient solution 5 which constitutes an electrolyte. Nutrient solution 5 is placed in a nutrient solution container 3. The potential of the nutrient solution 5 is maintained at a defined potential, such as a mass potential or potential Uq vis-à-vis the mass, by a reference electrode 4, e.g. a platinum electrode or hydrogen electrode.

The cell 2 is electrically coupled to an electronic circuit by a direct galvanic contact with a contact element 1 made of a conductive material, e.g. a metal that has a slight or negligible biological effect, such as, e.g., platinum, iridium, osmium or gold, or a doped monocrystalline or polycrystalline semiconductor such as conductive polysilicon; or a conductive synthetic material.

At point P, the contact element 1 is connected to a gate connection of gate FG of transistor T1, which has a second gate CG. Accordingly, transistor T1 is marked as a double-gate transistor. The first gate FG of the transistor is the inner gate. The second or outer gate CG is also known as control gate. The labelling as first and second gates follows the time sequence in producing a typical double-gate transistor. Source and drain connections of double-gate transistor T1 are marked with A and B respectively.

Without interpreting this as a restriction of the general approach, the figures indicate the reference potential as a mass potential M. It goes without saying that any other potential or reference voltage may be used alternatively without impairing the function of the array.

Below, the functional principle of the array according to the invention is described. Each membrane potential and each change in the membrane potential of cell 2 or the cell part placed on the contact area of contact element 1 is transmitted via contact element 1 to the first gate FG of double-gate transistor T1, and the said first gate is charged accordingly. Charging of the first gate FG influences the generation of a charge in the channel area between the source and drain of transistor T1, and in this manner triggers a change in the conductance/initial voltage. Such change of the channel properties may then be detected, evaluated and processed, in line with the field conditions, either via the current in the case of the voltage being held, or via the voltage drop in the case of fixed current.

Since the first gate FG is completely insulated within the electronic part of the coupling array according to the invention, the charge applied to it remains steady, with the exception of some minor leak current losses, and the charged state may be monitored, i.e. read out, at any time via its effect on the initial voltage and the conductivity of the channel of transistor T1.

In general, this electronic coupling array constitutes a kind of non-volatile storage cell that is charged, i.e. "written on" by the action potentials of cell 2. The charged state thus maps the action potentials of the cells. An evaluation of the conductances, currents and voltages derived therefrom generates a signal in the output circuit, which can be retrieved through a selection transistor T2 (see FIG. 3). In our context, this signal constitutes the "reading" of the action potentials.

In view of the output circuit being completely isolated from the input circuit, such reading is done without changing the input value, i.e. without any distinct effect on cell 2.

FIG. 1 shows a basic setup of the coupling array according to the invention. The live cell 2 is placed in a container 3 holding a nutrient solution 5, where the contact point of contact element 1 is represented schematically on the bottom of the container. This contact element 2 is connected at point P to the gate FG of the double-gate transistor T1. Cell 2 as the carrier and generator of the electric signal may be perceived as the source/generator Sz of signal impulses, as shown in the equivalent electric circuit diagram EZ of the cell in FIG. 2. The equivalent circuit diagram EZ also shows an internal resistor Rz of the cell. Within the meaning of the invention, the contact points of the contact elements 1 may generally be attached to any interfaces of the inside wall of container 3 that are within reach of or wetted or flushed by the nutrient solution 5. The source Uq is optional and is intended to demonstrate that the electrolyte potential of nutrient solution 5 may be different from mass potential M or the reference potential. The coupling array according to the invention as per FIG. 2 constitutes a read-out circuit. The biological cell acts as the signal source Sz which charges the first gate FG of the double-gate transistor T1.

Figure 2:
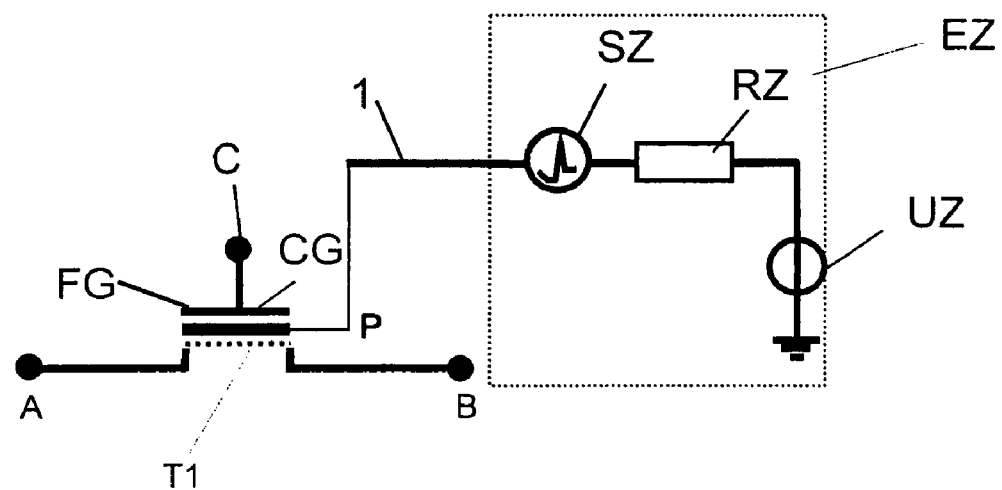
FIG. 2 shows the embodiment of FIG. 1 together with the equivalent circuit diagram of a coupled cell.
Figure 3:
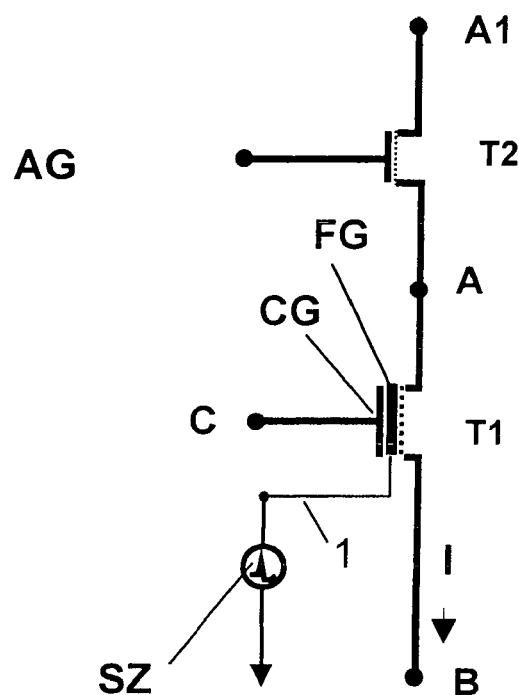
FIG. 3 shows the embodiment of the coupling array of FIG. 1 according to the invention with a series selection transistor.

FIG. 3 is a schematic representation of the option according to the invention to read out cell signals from the coupling circuit of FIG. 2. The circuit of FIG. 3 is particularly suitable to read out cell signals if the coupling circuit to the double-gate transistor T1 according to the invention is arrayed in the shape of a matrix. To this end, the double-gate transistor T1 is serially connected to a selection transistor T2 upstream of terminal A (between points A1 and A) which is selected through selection gate AG. The circuit functions as follows: If a voltage is applied between points A1 and B, no current will flow in this section for as long as the selection transistor T2 blocks it. If the selection transistor T2 opens, i.e. is opened by applying the requisite potential to selection gate AG, the current I flowing in the section A-B will depend on the voltage at terminal C of the control gate CG of the double-gate transistor T1 and also on the charge at the first gate FG of this transistor, which in turn depends on the "signal generator" Sz, i.e. the signal state of the biological cell. If the control gate CG switches on transistor T1, then the current I through the transistor will depend solely on the charge state of the first gate FG. The current I thus supplies a measure of the charge at the first gate FG, and thus of the signal state of the biological cell.

Figure 4:
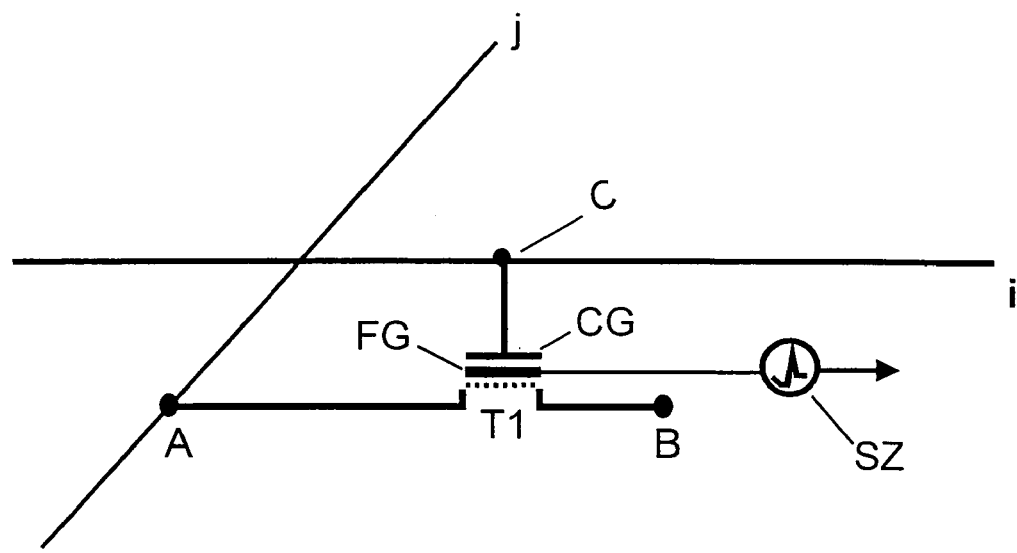
FIGS. 4 and 5 show matrix arrays of the coupling array according to the invention.
Figure 5:
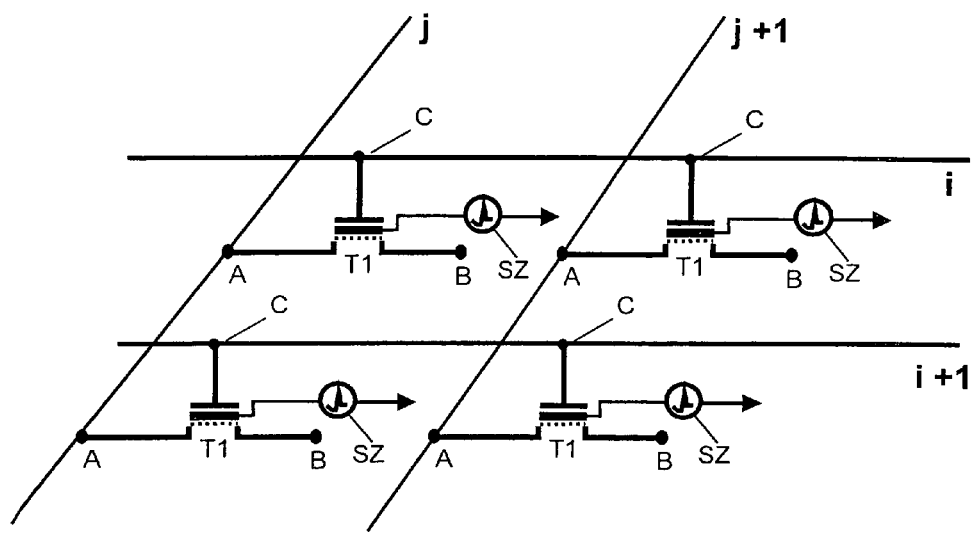

FIGS. 4 and 5 show an array of the coupling circuit according to the invention in the form of a matrix. Here, column address circuits j,j+1 are connected to the connection points A of a given double-gate transistor T1, and where—as shown in FIG. 3—a selection transistor not shown in the figures may be inserted. Line address circuits i,i+1 are connected to terminal C of the control gate CG (or may be connected to the selection gate of the selection transistor). The biological cells constitute a generator Sz for electric impulses.

Figure 6:
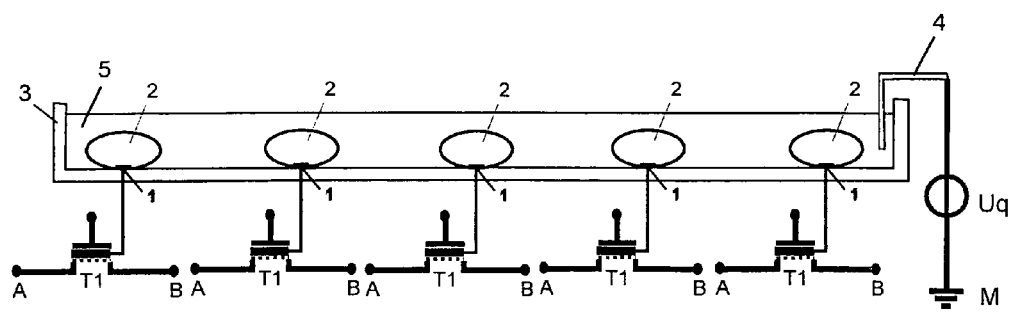
FIG. 6 shows several cells held in a nutrient solution container being coupled to coupling arrays according to the invention.
Figure 7A:
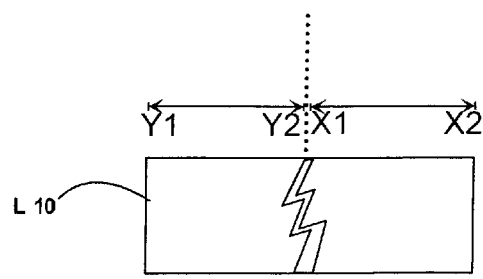
Figure 7B:
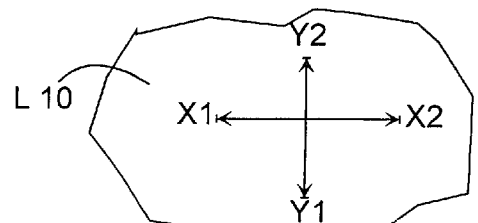
Figure 8A:
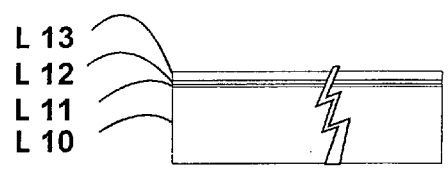
Figure 8B:
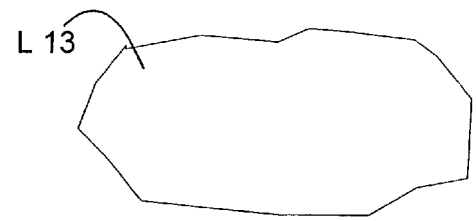
Figure 9A:
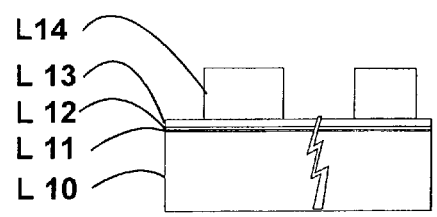
Figure 9B:
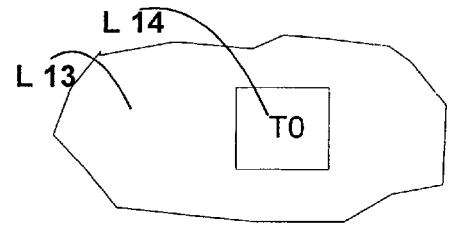

In order to demonstrate the robustness and error tolerance of the coupling array according to the invention, FIG. 6 shows the very general case of a multitude of coupling arrays according to the invention in the presence of a larger number of cells of false usage and cell failure. It can be easily seen that the absence of a cell (at 0) on a contact element 1 is easy to detect through the double-gate transistor T1. For as long as the double-gate transistor T1 (or a series-connected selection transistor) remains switched off, this contact element 1 on location 0 will remain ineffective. Similarly, a dysfunctional cell (2C) can be detected by showing no or an inadequate kind of stimulation/response pattern. This cell 2C may be similarly switched off without any problems through the associated double-gate transistor T1. Cells 2B, 2D and 2E show a satisfactory stimulation/response pattern, i.e. the cells respond actively/passively and thus indicate that the cell contact is fully functioning.

In summary it may be said that the array, through an appropriate addressing circuit and addressing processes (i.e. algorithms), allows excluding faulty contacts (0) and dysfunctional cells (2C) from further interaction without impairing interaction between the remaining cells (2B, 2D, 2E).

So far, the option to stimulate the biological cell has not yet been discussed. This option is provided by a special circuit designed so that the charge carrier is applied externally, i.e. for instance from the bulk of the double-gate transistor T1 either through so-called tunnelling, e.g. Fowler-Nordheim tunnelling, to the first gate FG to charge it, or through injecting so-called hot charge carriers from the channel area, or through injecting charge carriers from the control gate CG, each of which has the same effect of charging the first gate FG and thus stimulating the cell with an electric signal.

Without limitations and within the meaning of the array according to the invention, the container holding the nutrient solution and the cells may alternatively be applied directly to a semiconductor chip holding all or part of the electronic systems. In this case, the top layer (the so-called passivation) may be designed so that the contacts are attached to specific penetration points which are then put into contact with the cells.

Similarly, components with such contacts on the surface may be inserted directly into live tissue. In this case, a suitable, possibly integrated, contact needs to be provided for contacting the tissue liquid (electrolyte).

Below an embodiment of the coupling array according to the invention with a double-gate transistor is described.

The procedural steps are shown in FIGS. 7A to 33A as a cross-section and in FIGS. 7B to 33B as a so-called layout, where Figure numbers given below without the "A" and "B" indices are joint references to cross-section and layout.

On a substrate (layer 10) (see FIG. 7), which will generally be p-doped silicon, three layers are consecutively deposited or generated (FIG. 8): layer 11 (e.g. silicon dioxide), layer 12 (e.g. polysilicon), layer 13 (e.g. silicon nitride).

Figure 10A:
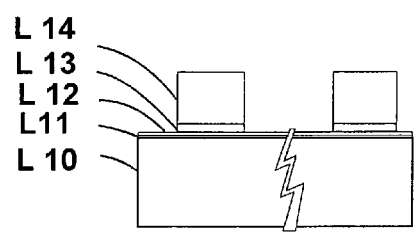
Figure 10B:
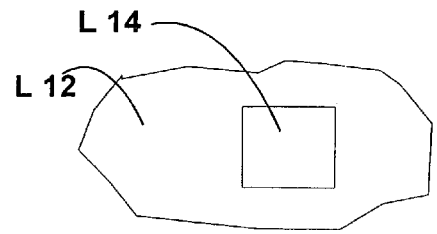
Figure 11A:
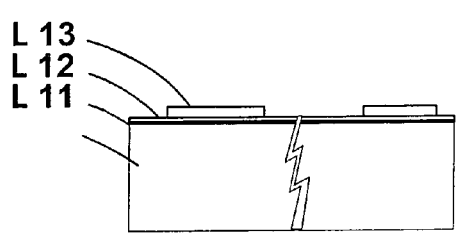
Figure 11B:
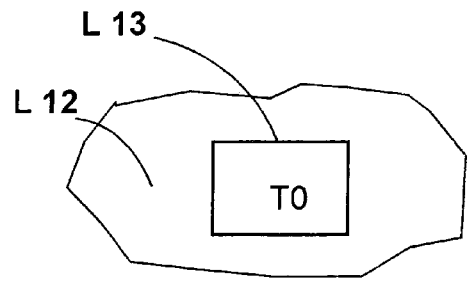

Next, using a photographic technique 1, the transistor T0 is defined across a lacquer mask (layer 14) (FIG. 9) and the area thus defined is created by etching layer 13 (FIG. 10).

Figure 12A:
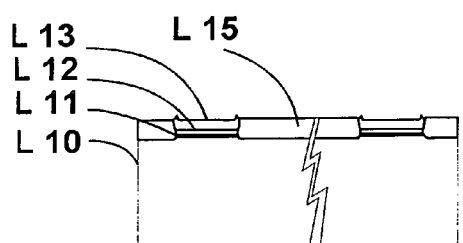
Figure 12B:
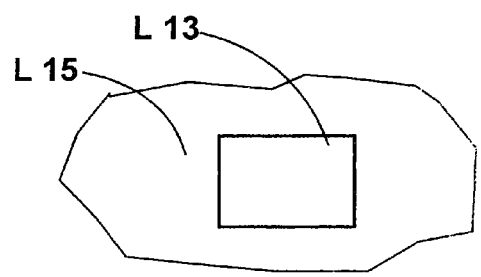

In the next step, the lacquer mask is removed (FIG. 11) and the area outside T0 is oxidised (LOCOS, local oxidation of silicon), in order to build the so-called field oxide area (layer 15) outside the transistor area T0 (FIG. 12). The field oxide area may alternatively be built by any other technique such as shallow trench isolation.

Figure 13A:
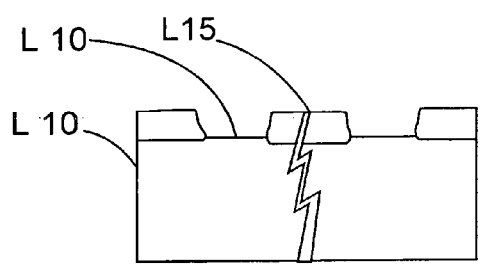
Figure 13B:
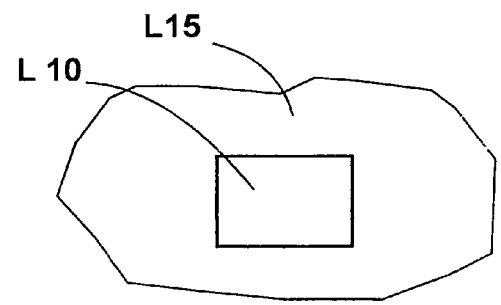
Figure 14A:
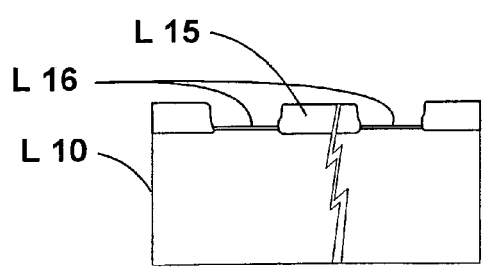
Figure 14B:
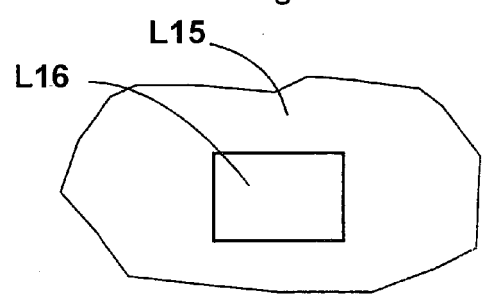
Figure 19A:
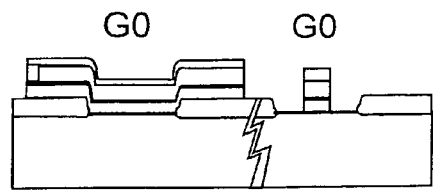
Figure 19B:
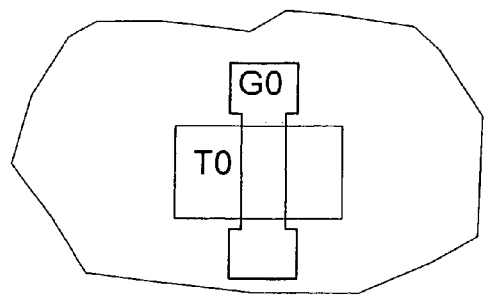

Following oxidation, the remains of layers 13, 12, 11 are removed (FIG. 13). If necessary, etching of a suitable kind is used to remove the residual oxide (e.g. native oxide), to expose the transistor area and build up the gate stack: after growing the first gate oxide (layer 16) (FIG. 14) or another suitable dielectric, a first polysilicon layer (layer 17) (FIG. 15) is either deposited in a doped condition or deposited without doping and subsequently doped (e.g. n-doped). Next, a thin silicon dioxide layer or other suitable dielectric (layer 18) is grown or deposited on this polysilicon layer, after which another layer, the so-called second polysilicon layer is deposited either in a doped condition or in an undoped condition and subsequently doped (layer 19) (FIG. 16).

On this layer, another dielectric layer (layer 20) is deposited or grown (e.g. silicon dioxide) (FIG. 17). In the next step (FIG. 18) gate G0 and the gate level are defined by photolithographic means (layer 21), and built by structurising layers 20, 19, 18, 17 and 16. With this procedure the first gate G1 (layer 17) and the second gate G2 (layer 19) are produced.

Figure 20A:
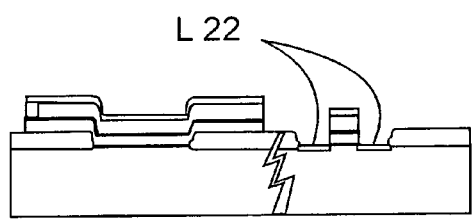
Figure 20B:
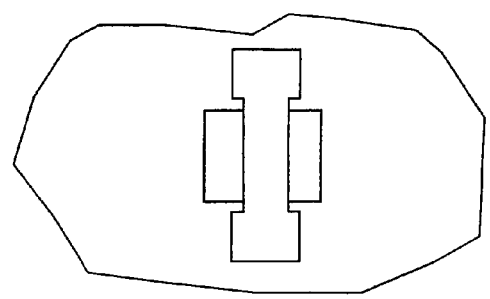
Figure 21A:
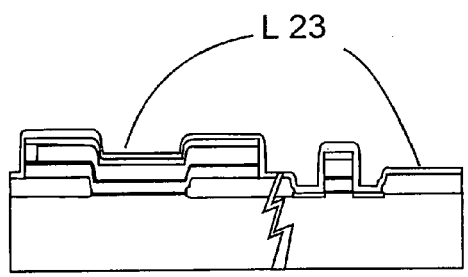
Figure 21B:
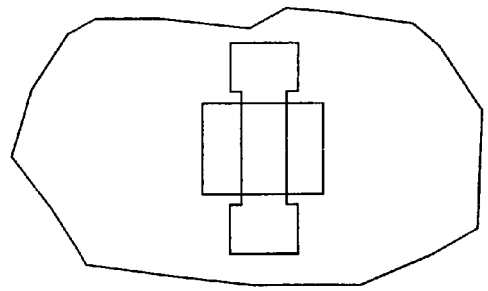
Figure 22A:
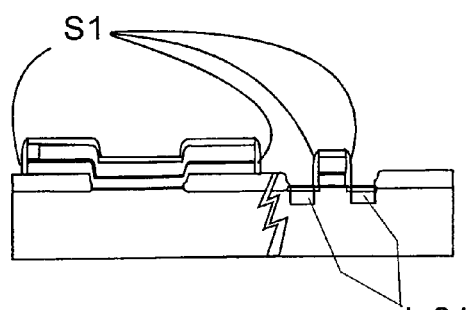
Figure 22B:
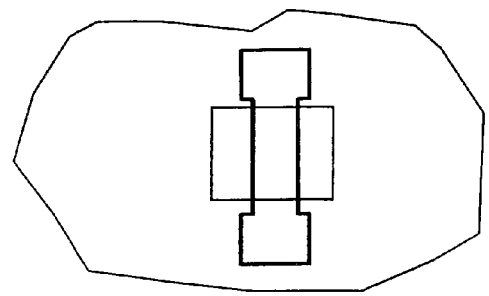
Figure 23A:
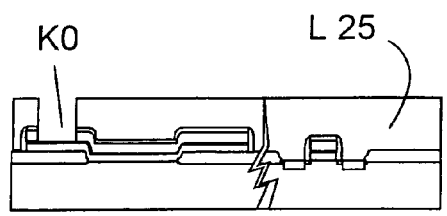
Figure 23B:
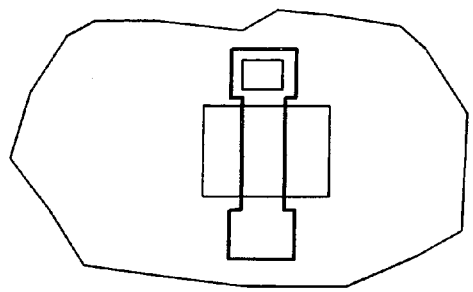

Next, the photolacquer (layer 21) is removed (FIG. 19) and, through an implantation process or other suitable doping process, the, so-called lightly doped drain (LLD) zone (layer 22) is produced self-adjusted (FIG. 20). In the next step, through conformous deposition of a dielectric (layer 23) (FIG. 21), followed by anisotropic etching-back, a so-called sidewall spacer (layer 24) is built (FIG. 22).

Figure 24A:
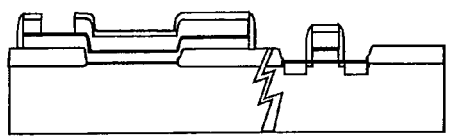
Figure 24B:
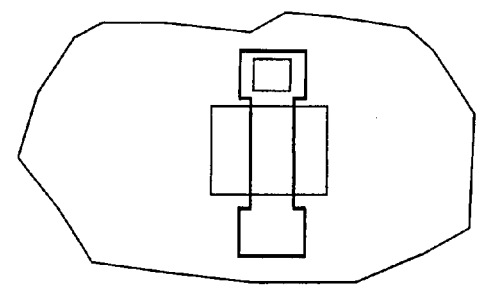
Figure 25A:
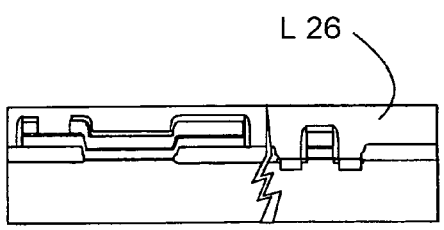
Figure 25B:
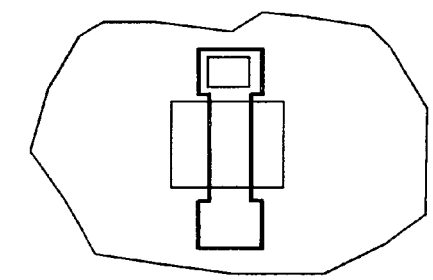
Figure 26A:
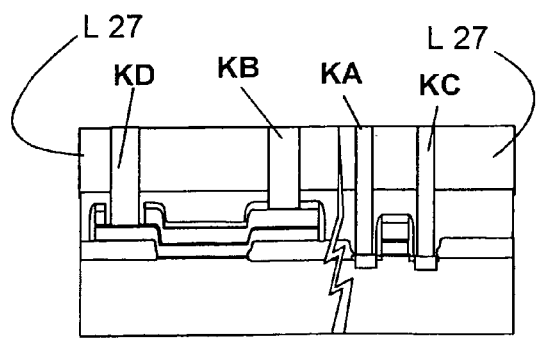
Figure 26B:
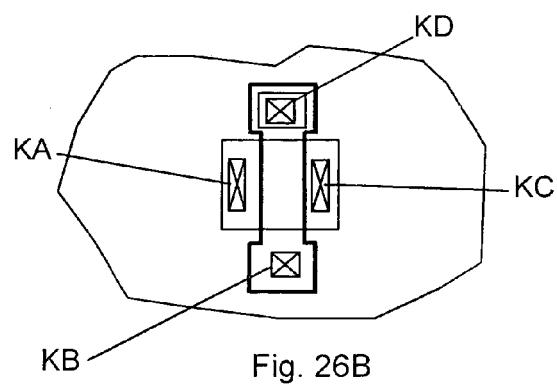

Once the spacer S1 has been built, the so-called heavily doped drain (HDD) implantation is performed (layer 25) (FIG. 23) and the source/drain connection area defined (FIG. 24).

In the embodiment shown, this HDD implantation is followed by defining the contact window (KO) by a photographic technique 3 (layer 26) (FIG. 25) and made by etching layers 20, 19 and, if necessary, 18. Upon removing the lacquer (layer 26), a thick dielectric single or multiple layer (FIG. 26) is deposited and if necessary levelled or deposited in a level state (layer 27).

Next, contact holes KA, KB, KC, KD (layer 28) (FIG. 27) are defined by a photographic technique 4, and openings ranging to source, drain, gate 1 and gate 2 are made by etching the respective layers.

If necessary a barrier layer (layer 29) (FIG. 28) is used to fill the contact holes with a conductive material (e.g. tungsten/titanium nitride) (layer 30) (FIGS. 29 and 30).

As the next step, a metallic layer (layer 31) is applied (FIG. 31) and structured using a photographic technique 5. Upon completion of the metallisation layer M1 (layer 31), one, two or more dielectric layers are applied to the embodiment, which are either level or levelled (in FIG. 31 two layers, layer 32 and layer 33).

Figure 31A:
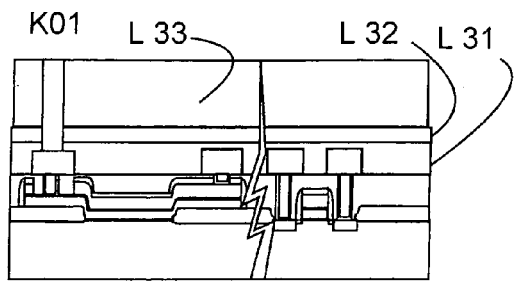
Figure 31B:
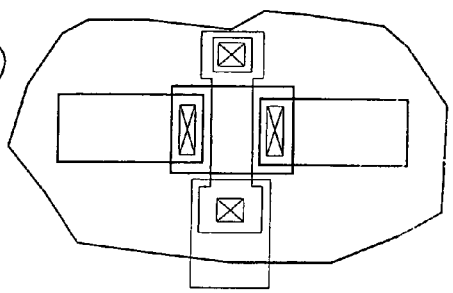
Figure 32A:
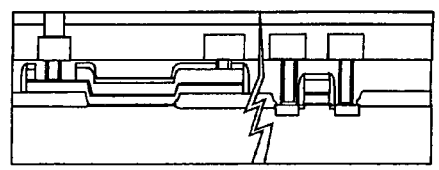
Figure 32B:
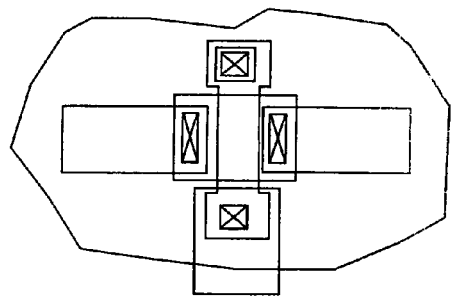
Figure 33A:
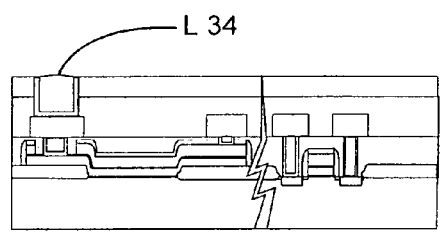
Figure 33B:
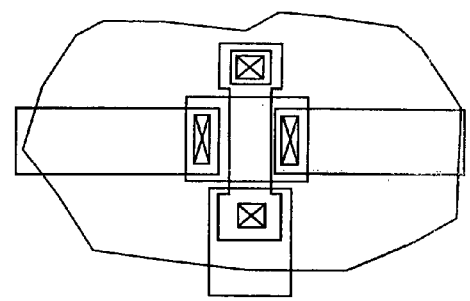
Figure 34A:
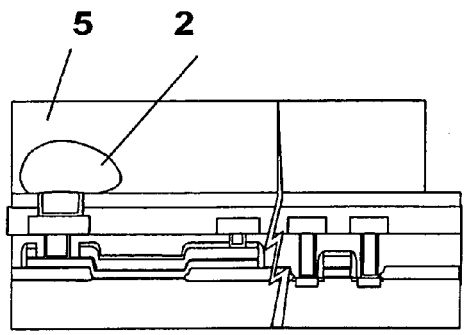
Figure 34B:
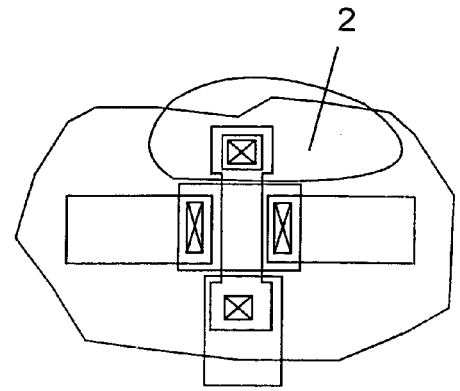
Figure 39A:
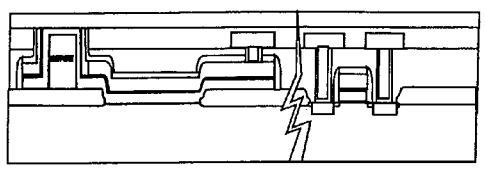
Figure 39B:
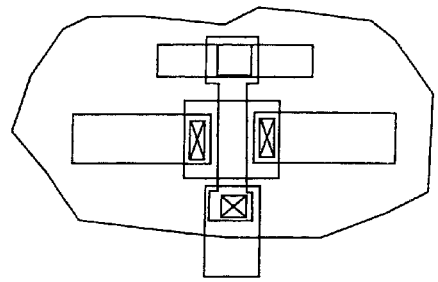
Figure 40A:
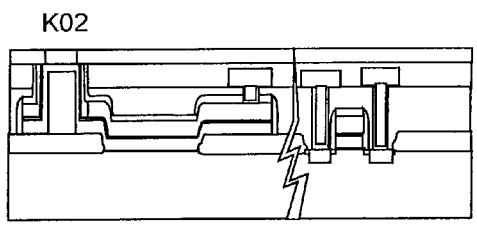
Figure 40B:
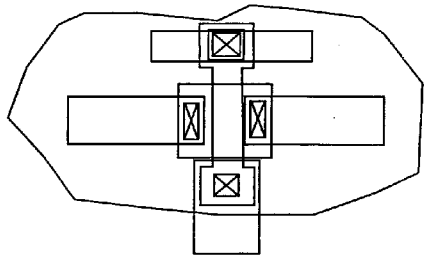
Figure 41A:
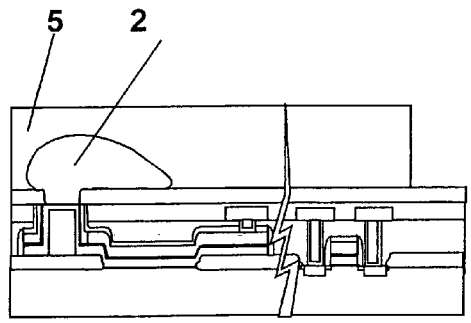
Figure 41B:
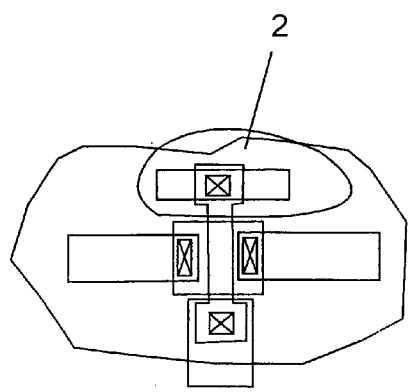

Upon depositing these layers, which are chiefly provided to chemically and electrically insulate (passivate) the transistor area including its metallisation from its environment, a photolithographic process 6 (layer 33) is used to define a contact hole K01 to gate 1, which is then built by etching (FIGS. 31 and 32). Next, the photolithographic lacquer (layer 34) is removed and the remaining contact hole K01 is filled with a barrier/adhesive layer (layer 35) and a conductive material (layer 36) (FIG. 33), so that the surface will remain essentially level. This contact area provides for the coupling to a biological cell according to the invention (FIGS. 34A (cross-section) and 34B (layout)). As seen from FIG. 34, the cell contact can be made directly through this docking point. The figure described here will be perceived as Version A.

In a Version B, this contact, as shown in FIGS. 35A, 35B, may be produced in a single step right through gate 2 without limiting the invention. For this purpose, the contact hole etching must be made after the integrated circuit has been fully completed. For the sake of simplicity, an adhesive/barrier layer which may be present has not been expressly drawn.

In a Version C of the invention, the cell contact can be made without using a metallic interface, as shown in FIG. 36.

In a Version D, shown in FIGS. 38A to 41A as a cross-section and in FIGS. 38B to 41B as a layout, gate 1, or a feeder to it, can be run directly to the surface by introducing a so-called support level (for its manufacturing process see FIG. 37) which produces a barrier in its core (layer 37). For this, only the conformity of the polysilicon deposit and the dielectrics is used.

For making the contacts, a lithographic step is required same as in Versions B, C and D, which allows making a contact K02 to gate 1 or its feeder. Actual contacting of the cell is then done as in Version C. Within the meaning of the invention, contact hole filling may be used alternatively.

The invention claimed is:

1. Array to couple a live cell, in particular a nerve cell, to an electronic circuit to pick up directly or indirectly electrically effective cell signals and/or to electrically stimulate the cell, wherein the coupling array comprising a transistor with a double gate, including a first gate designed as a control gate to select the transistor via external control signals, and a second gate designed as a floating gate, which is connected to an electrically conducting contact element which can be attached to the cell in order to register changes in the electric properties of the cell.

2. Coupling array as claimed in claim 1, wherein a container to hold a nutrient solution is provided, where at least one contact element either projects into the container or at least partly forms this container.

3. Coupling array as claimed in claim 2, wherein an electrically conducting reference electrode is provided connected to a reference voltage, where the reference electrode projects into the interior of the container holding the nutrient solution.

4. Coupling array as claimed in claim 1, wherein the electrically conductive contact element is made of a material of low biological effect, preferentially chosen from refractory metals, such as platinum, iridium, osmium, tungsten or gold, or alloys thereof; or of semiconductor silicides, such as platinum silicide, tungsten silicide, titanium silicide; or of a doped monocrystalline or polycrystalline semiconductor, such as conductive polysilicon; or of conductive plastics.

5. Coupling array as claimed in claim 1, where a large number of coupling arrays are arrayed in the form of a matrix of lines and columns, wherein each coupling array can be selected by an address circuit singly or in groups through activating column and line address circuits.

6. Coupling array as claimed in claim 5, wherein each coupling array has a selection switch with a control connection, in particular a selection transistor with a selection gate, where the input of the selection switch is connected to a line address circuit and the control connection of the selection switch is connected to a column address circuit.

7. Coupling array as claimed in claim 6, wherein the address circuit has address evaluation tools to detect dysfunctional cells and faulty contacts between contact element and cell, where in the case of such detection further interaction between these cells and contact elements can be selectively interrupted.

8. Coupling array as claimed in claim 7, wherein interrupting tools such as an electronic switch are provided for the selective interruption of interaction between cells.

9. Coupling array as claimed in claim 1, wherein a multiple number of coupling arrays are arrayed on a chip, where the chip is preferentially produced by the Si-planar process and may be integrated with other technologies, such as circuits for local amplification, on-chip logic or systems on chips.

10. Coupling array as claimed in claim 9 wherein a container to hold a nutrient solution is provided, where at least one contact element either projects into the container or at least partly forms this container, and wherein the container holding the nutrient solution is placed on the chip.

11. Coupling array as claimed in claim 1, wherein the second gate of the double-gate transistor connected with the electrically conducting contact element can be charged with external chargers.

12. Coupling array as claimed in claim 11, wherein for charging with external chargers of the second gate connected with the electrically conducting contact element tunneling is provided, e.g. Fowler Nordheim tunnels, between the gate and the bulk area of the double-gate transistor, or injection of hot charge carriers from the channel area of the double-gate transistor, or injection of charge carriers from the first gate of the double-gate transistor.

* * * * *